United States Patent [19]

Haga et al.

[11] Patent Number: 4,504,665
[45] Date of Patent: Mar. 12, 1985

[54] PROCESS FOR PRODUCING CHLORONICOTINIC ACID COMPOUNDS

[75] Inventors: Takahiro Haga, Kusatsu; Tohru Koyanagi, Kyoto; Toshio Nakajima, Moriyama; Takeshi Ohshima, Kusatsu, all of Japan

[73] Assignee: Ishihara Sangyo Kaisha Ltd., Osaka, Japan

[21] Appl. No.: 482,535

[22] Filed: Apr. 6, 1983

[30] Foreign Application Priority Data

Apr. 12, 1982 [JP] Japan ................................. 57-60688
Sep. 8, 1982 [JP] Japan ................................. 57-156335

[51] Int. Cl.$^3$ ............................................ C07D 213/55
[52] U.S. Cl. ...................................... 546/318; 546/320
[58] Field of Search ................................ 546/318, 320

[56] References Cited

U.S. PATENT DOCUMENTS 4,144,238  3/1979  Said ..................................... 546/313

FOREIGN PATENT DOCUMENTS 2415748 10/1974  Fed. Rep. of Germany ...... 546/320
169672 12/1981  Japan ................................. 546/313

OTHER PUBLICATIONS

Chemical Abstracts, vol. 84, No. 17, Apr. 26, 1976, p. 521, Abstract No. 121614w.

Primary Examiner—Alan L. Rotman
Attorney, Agent, or Firm—Oblon, Fisher, Spivak, McClelland & Maier

[57] ABSTRACT

A chloronicotinic acid compound is prepared by hydrolyzing a 3-trichloromethyl pyridine compound in the presence of sulfuric acid or phosphoric acid. By this process, a highly pure chloronicotinic acid compound is obtainable in good yield. This compound is useful as an intermediate for medicines.

6 Claims, No Drawings

PROCESS FOR PRODUCING CHLORONICOTINIC ACID COMPOUNDS

The present invention relates to a process for producing chloronicotinic acid compounds (hereinafter referred to simply as CNA) which are useful as an intermediate for medicines.

Heretofore, various processes have been proposed for the production of CNA. For instance, the following processes have been proposed for the production of 2-chloronicotinic acid:

(1) a process which comprises reacting nicotinic acid N-oxide with phosphorus oxychloride and triethylamine, distilling 2-chloronicotinic acid chloride from the reaction mixture and hydrolyzing the distillate thereby obtained (U.S. Pat. No. 4,144,238); and (2) a process which comprises reacting 3-cyanopyridine N-oxide with phosphorus oxychloride to form 2-chloro-3-cyanopyridine which is then hydrolyzed (Japanese Unexamined Patent Publication No. 169672/1981).

However, these processes have various drawbacks. Namely, the process (1) has drawbacks such that it is necessary to use irritative phosphorus oxychloride as a chlorinating agent; since isomers form during the chlorination, it is necessary to carry out purification prior to the hydrolysis; and since 2-chloronicotinic acid chloride is unstable during the purification, a due care is required for its handling. On the other hand, the process (2) has drawbacks such that 3-cyanopyridine is expensive; phosphorus oxychloride is difficult to handle; during the chlorination, isomers will form; and a cumbersome operation is required to separate the desired product by adding an acid after the hydrolysis with an alkali.

Accordingly, it is an object of the present invention to overcome the above-mentioned difficulties and to provide an improved process for the production of CNA.

The present invention provides a process for producing CNA represented by the general formula

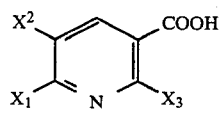
(I)

where each of $X_1$, $X_2$ and $X_3$ is a hydrogen atom or a chlorine atom and at least one of $X_1$ and $X_3$ is a chlorine atom, which comprises hydrolyzing a trichloromethyl pyridine compound (hereinafter referred to simply as TCP) represented by the general formula

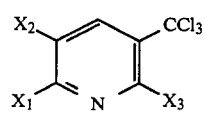
(II)

where $X_1$, $X_2$ and $X_3$ are as defined above, in the presence of sulfuric acid or phosphoric acid.

Further, the present invention provides a process for producing CNA of the general formula I which comprises reacting a trifluoromethyl pyridine compounds (hereinafter referred to simply as TFP) represented by the general formula

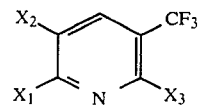
(III)

where $X_1$, $X_2$ and $X_3$ are as defined above, with aluminum chloride to obtain TCP of the general formula II and hydrolyzing TCP in the presence of sulfuric acid or phosphoric acid.

Now, the present invention will be described in detail with reference to the preferred embodiments.

Chlorination step:

According to the process of the present invention, TFP may be reacted with aluminum chloride in the absence of a solvent. However, for an industrial operation, it is preferred that they are reacted in a solvent. As TFP to be used in the process of the present invention, there may be mentioned 2-chloro-3-trifluoromethyl pyridine (melting point 39.1° C.), 6-chloro-3-trifluoromethyl pyridine (melting point: 30.2° C.), 2,5-dichloro-3-trifluoromethyl pyridine (boiling point: 119° to 121° C./90 mm Hg), 2,6-dichloro-3-trifluoromethyl pyridine (melting point: 6.0° to 6.5° C.), 5,6-dichloro-3-trifluoromethyl pyridine (melting point: 9° to 10° C.) and 2,5,6-trichloro-3-trifluoromethyl pyridine (melting point: 48° to 50° C.). As the solvent, there may be mentioned a halogenated hydrocarbon such as methylene chloride, chloroform, F-112 ($CFCl_2.CFCl_2$) or ethylene chloride, and an aromatic hydrocarbon having an electron attractive group such as monochlorobenzene, dichlorobenzene, trichlorobenzene or nitrobenzene. Aluminum chloride is used usually in an amount of from 0.5 to 5 mols, preferably from 1 to 3 mols, more preferably from 1 to 1.5 mols, per mol of TFP. Aluminum chloride may be added in one portion. However, it is preferred to add it portionwise to permit the reaction proceeds uniformly. The reaction temperature may optionally be selected usually within a range of from 30° to 180° C., preferably from 50° to 130° C. The reaction time is usually from 0.5 to 10 hours.

The reaction product obtained by the above reaction is cooled and then introduced into ice water, and then TCP may be obtained by usual extraction with a solvent or by distillation. However, it is industrially more advantageous that the above reaction product is introduced into water, subjected to liquid phase separation to remove aluminum compounds and then subjected to the subsequent reaction.

As TCP to be used in the process of the present invention, there may be mentioned 2-chloro-3-trichloromethyl pyridine, 6-chloro-3-trichloromethyl pyridine, 2,5-dichloro-3-trichloromethyl pyridine, 2,6-dichloro-3-trichloromethyl pyridine, 5,6-dichloro-3-trichloromethyl pyridine and 2,5,6-trichloro-3-trichloromethyl pyridine.

Hydrolysis step:

Then, TCP is hydrolyzed in the presence of sulfuric acid or phosphoric acid to obtain CNA. As CNA, there may be mentioned 2-chloronicotinic acid (melting point: 196° to 198° C.), 6-chloronicotinic acid (melting point: 199° to 201° C.), 2,5-dichloronicotinic acid (melting point: 152° to 155° C.), 2,6-dichloronicotinic acid (melting point: 148° to 150° C.), 5,6-dichloronicotinic acid (melting point: 166° to 168° C.), and 2,5,6-trichloronicotinic acid (melting point: 150° to 154° C.). Sulfuric acid is used usually in an amount of from 1 to 100 mols, preferably from 2 to 30 mols, per mol of TCP. The concentration of the sulfuric acid is usually from 1 to 100%, preferably from 30 to 100%, more preferably from 40 to 100%. The reaction temperature for the hydrolysis is usually from 50° to 150° C., preferably from 80° to 130° C. The reaction time is usually from 0.5 to 30 hours. When phosphoric acid is used, the amount of phosphoric acid is usually from 1 to 100 mols, preferably from 2 to 30 mols, per mole of TCP. The concentration of the phosphoric acid is usually from 10 to 100%, preferably from 30 to 100%, more preferably from 40 to 100%. The reaction temperature for the hydrolysis is usually from 50° to 150° C., preferably from 80° to 130° C. Further, the reaction time is usually from 0.5 to 30 hours. In the actual operation of the process of the present invention, it is necessary to select optional conditions from these reaction conditions. Namely, in this hydrolysis, if sulfuric acid or phosphoric acid having a low concentration is used, if the reaction temperature is relatively high or it the reaction time is prolonged, desired CNA once formed is likely to be converted into a by-product, which is substituted by a hydroxyl group at the α-position, such as 2-hydroxynicotinic acid, and therefore it is necessary to take a due care. In order to avoid this side reaction as far as possible, it is preferred, for instance, that when the reaction is conducted at 100° C. with use of 50% sulfuric acid, the reaction time is about 2 hours; when the reaction is conducted at 100° C. with use of 60% sulfuric acid, the reaction time is from about 7 to about 8 hours; and when the reaction is conducted at a temperature of from 110° to 120° C. with use of 100% sulfuric acid, the reaction time is about 2 hours. Likewise, it is preferred that when the reaction is conducted at 90° C. with use of 70% phosphoric acid, reaction time is from 1 to about 3 hours and when the reaction is conducted at 90° C. with use of 100% phosphoric acid, the reaction time is about 3 hours.

The reaction product obtained by the above reaction is cooled and then subjected to usual operations such as filtration, washing and purification, whereby CNA having a high purity can be obtained.

According to the process of the present invention, the following advantages are obtainable.

(1) TFP of the general formula III to be used as a starting material is readily and economically available since it is industrially produced.

(2) In this process, side reactions do not substantially take place and TCP as the intermediate is stable, whereby the desired product can be obtained in good yield and with a high purity.

(3) The reaction is simple and easy, and the reaction time is short.

Now, the process of the present invention will be described in further detail with reference to Examples.

EXAMPLES 1 TO 5

Chlorination step

To 18.2 g of 2-chloro-5-trifluoromethyl pyridine, 20 g of aluminum chloride was added in 2 hours, and they were reacted under the predetermined reaction conditions as shown in Table 1. After the completion of the reaction, the reaction product was cooled and then introduced into ice water, and the oil layer was separated by liquid separation. The solvent was removed by distillation to obtain 2-chloro-5-trichloromethyl pyridine.

TABLE 1

| | Solvent | | Reaction temp. (°C.) | Reaction time (hr) | 2-chloro-5-CCl$_3$ pyridine | |
|---|---|---|---|---|---|---|
| | Kind | Amount (ml) | | | Amount (g) | Yield (%) |
| Exp. 1 | Trichlorobenzene | 30 | 100 | 3.5 | 21.1 | 92 |
| Exp. 2 | Dichloroethane | 50 | 85 | 4 | 20.8 | 90 |
| Exp. 3 | o-dichlorobenzene | 30 | 100 | 2 | 21.0 | 91 |

Hydrolysis step

A mineral acid was added to 20 g of 2-chloro-5-trichloromethyl pyridine, and the mixture was reacted under stirring under the predetermined conditions as shown in Table 2. After the completion of the reaction, the reaction product was introduced into ice water, and the precipitated crystals were filtered, washed and then purified with a mixed solvent of water and acetonitrile (ratio=1:1) whereby the results as shown in Table 2 were obtained.

TABLE 2

| | Mineral acid | | Reaction condition | | 2-chloronictinic acid | | |
|---|---|---|---|---|---|---|---|
| | Kind | Amount (ml) | Reaction temp. (°C.) | Reaction time (hr) | Amount (g) | Yield (%) | Purity (%) |
| Exp. 4 | 50% sulfuric acid | 120 | 100 | 2 | 8.7 | 64 | 99 |
| Exp. 5 | 60% sulfuric acid | 120 | 100 | 7 | 9.8 | 72 | 99 |

EXAMPLE 6

Hydrolysis step 5 g of 2-chloro-5-trichloromethyl pyridine was dissolved in 30 g of concentrated sulfuric acid, and the solution was heated to 110° C., whereupon hydrogen chloride gas was vigorously generated. The reaction was conducted at a temperature of from 110° to 120° C. for 2 hours. After the completion of the reaction, the reaction product was introduced into ice water, whereupon white crystals precipitated. The crystals were filtered, washed and dried to obtain 3.2 g of 6-chloronicotinic acid (yield: 94%, purity: 95%).

EXAMPLE 7

Chlorination step—Hydrolysis step 18.2 g of 2-chloro-3-trifluoromethyl pyridine was dissolved in 30 ml of trichlorobenzene, and 20 g of aluminum chloride was added thereto in 2.5 hours at 100° C. The mixture was reacted for 4 hours. After the completion of the reaction, the reaction product was cooled and then introduced in ice water, and the oil layer was separated by liquid separation. To this oil layer, 120 ml of 60% sulfuric acid was added, and the mixture was reacted at 100° C. for 8 hours under stirring. After the completion of the reaction, the reaction product was introduced into ice water and the crystals thereby precipitated were filtered, washed and purified with use of a mixed solvent of water and acetonitrile (ratio=1:1), whereupon 8.5 g of 2-chloronicotinic acid (yield: 54%, purity: 99%) was obtained.

EXAMPLES 8 TO 12 AND COMPARATIVE EXAMPLES 1 TO 3

Chlorination Step

Under the conditions as shown in Table 3, a trifluoromethyl pyridine compounds and aluminum chloride were mixed and reacted. After the completion of the reaction, the reaction product was cooled, then introduced into ice water and extracted by adding methylene chloride. Then, the starting materials and the trichloromethyl pyridine compounds thereby formed were separated with use of hot n-hexane.

TABLE 3

| | Trifluoromethyl pyridine compound | | Amount of AlCl₃ (g) | Reaction conditions | | Trichloromethyl pyridine compound | | |
|---|---|---|---|---|---|---|---|---|
| | Kind | Amount (g) | | Reaction initiating temp. (°C.) | Time (hr.) | Kind | Obtained amount (g) | Yield (%) |
| Exp. 8 | 2-chloro-3-trifluoromethyl pyridine | 36.4 | 40 | 40 | 0.5 | 2-chloro-3-trichloromethyl pyridine | 17 | 65* |
| Exp. 9 | 2-chloro-3-trifluoromethyl pyridine | 5.4 | 4 | 70 | 2.5 | 2-chloro-3-trichloromethyl pyridine | 3.3 | 73 |
| Exp. 10 | 2-chloro-3-trifluoromethyl pyridine | 18.2 | 20 | 70 | 1 | 2-chloro-3-trichloromethyl pyridine | 16 | 69 |
| Exp. 11 | 2,6-dichloro-5-trifluoromethyl pyridine | 10.8 | 10 | room temp. | 0.5 | 2,6-dichloro-3-trichloromethyl pyridine | 5.8 | 77 |

*The yield represents a yield based on the consumed trifluoromethyl pyridine compound.

Hydrolysis step

As shown in Table 4, a mineral acid was added to a trichloromethyl pyridine compound, the mixture was reacted under stirring. After the completion of the reaction, the reaction product was introduced into ice water, then filtered and washed, whereupon the results as shown in Table 4 were obtained.

TABLE 4

| | Trichloromethyl pyridine compound | | Mineral acid | | Reaction conditions | | Chloronicotinic acid compound | | | |
|---|---|---|---|---|---|---|---|---|---|---|
| | Kind | Amount (g) | Kind | Amount (ml) | Temp. (°C.) | Time (hr.) | Kind | Obtained amount (g) | Yield (%) | Purity (%) |
| Exp. 12 | 2-chloro-3-trichloromethyl pyridine | 1.5 | 100% phosphoric acid | 20 | 90 | 3 | 2-chloronicotinic acid | 0.86 | 84 | 94 |
| Comparative Exp. 1 | 2-chloro-3-trichloromethyl pyridine | 3.0 | 37% hydrochloric acid | 20 | 100 | 3 | mixture of 2-chloronicotinic acid and 2-hydroxynicotinic acid | 0.83 | 21 | 52 |
| Comparative Exp. 2 | 2-chloro-3-trichloromethyl pyridine | 1.5 | 69% nitric acid | 20 | 100 | 2 | mixture of 2-chloronicotinic acid, 2-hydroxy nicotinic acid and unknown substance | 0.6 | 59 | 80 |
| Comparative Exp. 3 | 2-chloro-3-trichloromethyl pyridine | 5 | 10% nitric acid | 20 | 100 | 2 | mixture of 2-chloronicotinic acid, 2-hydroxy nicotinic acid and unknown substance | 2.2 | 65 | 60 |

We claim:

1. A process for producing a chloronicotinic acid compound represented by the general formula

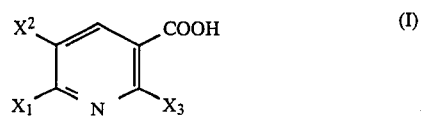

(I)

where each of $X_1$, $X_2$ and $X_3$ is a hydrogen atom or a chlorine atom and at least one of $X_1$ and $X_3$ is a chlorine atom, which comprises hydrolyzing at a temperature of 80°–130° C. a trichloromethyl pyridine compound represented by the general formula

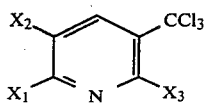 (II)

where $X_1$, $X_2$ and $X_3$ are as defined above, in the presence of sulfuric acid or phosphoric acid having a concentration of from 40 to 100%, said acid being present in an amount of from 2–30 mols per mol of the trichloromethyl pyridine compound.

2. The process according to claim 1 wherein 2-chloronicotinic acid is produced by hydrolyzing 2-chloro-3-trichloromethyl pyridine in the presence of sulfuric acid or phosphoric acid.

3. The process according to claim 1 wherein 6-chloronicotinic acid is produced by hydrolyzing 6-chloro-3-trichloromethyl pyridine in the presence of sulfuric acid or phosphoric acid.

4. A process for producing a chloronicotinic acid compound represented by the general formula

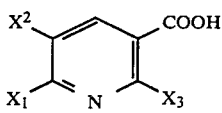 (I)

where each of $X_1$, $X_2$ and $X_3$ is a hydrogen atom or a chlorine atom and at least one of $X_1$ and $X_3$ is a chlorine atom, which comprises reacting 1 mol of trifluoromethyl pyridine compound represented by the general formula

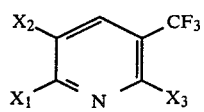 (III)

where $X_1$, $X_2$ and $X_3$ are as defined above, with 1–3 mols of aluminum chloride at a temperature of 50°–130° C. to obtain a trichloromethyl pyridine compound represented by the general formula

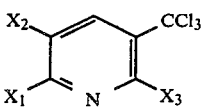 (II)

where $X_1$, $X_2$ and $X_3$ are as defined above, and then hydrolyzing at a temperature of 80°–130° C. the trichloromethyl pyridine compound of the general formula II in the presence of sulfuric acid or phosphoric acid having a concentration of from 40 to 100%, said acid being present in an amount of from 2–30 mols per mol of the trichloromethyl pyridine compound.

5. The process according to claim 4 wherein 2-chloronicotinic acid is produced by reacting 2-chloro-3-trifluoromethyl pyridine with aluminum chloride to obtain 2-chloro-3-trichloromethyl pyridine and then hydrolyzing the 2-chloro-3-trichloromethyl pyridine in the presence of sulfuric acid or phosphoric acid.

6. The process according to claim 4 wherein 6-chloronicotinic acid is produced by reacting 6-chloro-3-trifluoromethyl pyridine with aluminum chloride to obtain 6-chloro-3-trichloromethyl pyridine and then hydrolyzing the 6-chloro-3-trichloromethyl pyridine in the presence of sulfuric acid or phosphoric acid.

* * * * *